United States Patent
Jacobs et al.

(10) Patent No.: US 6,811,976 B1
(45) Date of Patent: Nov. 2, 2004

(54) METHOD OF DIAGNOSING AND SCREENING FOR MALE INFERTILITY THROUGH MUTATIONS IN POLG

(75) Inventors: Howard Jacobs, Tampere (FI); Anja Rovio, Kangasala (FI)

(73) Assignee: Licentia Oy, Helsinki (FI)

( * ) Notice: Subject to any disclaimer, the term of this patent is extended or adjusted under 35 U.S.C. 154(b) by 0 days.

(21) Appl. No.: 09/913,954

(22) PCT Filed: Feb. 22, 2000

(86) PCT No.: PCT/FI00/00140

§ 371 (c)(1),
(2), (4) Date: Dec. 4, 2001

(87) PCT Pub. No.: WO00/50629

PCT Pub. Date: Aug. 31, 2000

(30) Foreign Application Priority Data

Feb. 22, 1999 (FI) ................................. 990380

(51) Int. Cl.[7] .......................... C12Q 1/68; C12P 19/34; C07H 21/02; C07H 21/04
(52) U.S. Cl. ........................ 435/6; 435/91.2; 536/23.5; 536/24.31; 536/24.33
(58) Field of Search .......................... 435/6, 91.1, 91.2; 536/23.1, 23.5, 24.31, 24.33

(56) References Cited

PUBLICATIONS

Rovio et al. Euro. Jrnl. of HUman Genetics (1999) 7, 140–146.*
Ropp and Copeland Genomics (1996) 36, 449–458.*
Rovia A et al: "Analysis of the trinucleotide CAG repeat from the human mitochondrial DNA polymerase gene in healthy and diseased individuals" European Journal of Human Genetics. vol. 7, 1999, pp. 140–146.
Database Dialog Inform Services [Online] file 34; Barrati Clr et al: "Diagnostic tools in male infertility" retrieved from DIALOG, accession No. 06789473, SciSearch acc. No. Genuine Art.: ZR801 & Human Reproduction, vol. 3, No. 1, Apr. 1998, pp. 51–61.
Database Dialog Information Servo [Online] File 34, SciSearch(R); Ruizpesini E et al: Correlation of sperm motility with mitochondrial enzymatic activities retrieved from Dialog Inf.Serv., accession No. 06953993/25; Genuine Art. 107QW & Clinical Chemistry, vol. 44, No. 8, Aug. 1998, pp. 1616–1620.
Ropp Ph A et al: "Cloning and characterization of the human mitochondrial DNA polymerase, DNA polymerase ganma" GENOMICS, vol. 36, 1996, pp. 449–458.
Wang Q et al.: "Analysis of the Transactivation Domain of the Androgen Receptor in Patients with Male Infertility" Clinical Genetics 1998: 34, pp. 185–192.
Eu L. Yong et al.; "Androgen Receptor Transactivation Domain and Control of Spermatogenesis" Department of Obstetrics and Gynaecology, National University of Singapore, 1998 Journals of Reproduction and Fertility pp. 141–144.

* cited by examiner

*Primary Examiner*—Carla J. Myers
*Assistant Examiner*—Sally Sakelaris
(74) *Attorney, Agent, or Firm*—Nixon & Vanderhye P.C.

(57) ABSTRACT

The present invention relates to a novel diagnostic method for the detection of infertility in males. In particular, the present invention relates to a diagnostic method for detecting the presence or absence of a mutation or mutations in the POLG gene encoding mitochondrial DNA polmerase in a biological sample. The invention relates also to the use of a mutant POLG gene in the detection of infertility in males and in the screening of human populations for the presence of such mutation or mutations as a predictive test for male infertility. The invention also relates to the use of the POLG gene as an indicator of other pathological conditions associated with or related to male infertility, including those manifesting in women.

20 Claims, 1 Drawing Sheet

METHOD OF DIAGNOSING AND SCREENING FOR MALE INFERTILITY THROUGH MUTATIONS IN POLG

This is a national stage application under 35 U.S.C. 371 of PCT/FI00/00140, filed Feb. 22, 2000, now abandoned.

FIELD OF THE INVENTION

The present invention relates to a novel diagnostic method for the detection of infertility in males. In particular, the present invention relates to a diagnostic method for detecting the presence or absence of a mutation or mutations in the POLG gene in a biological sample. The invention relates also to the use of a mutant POLG gene in the detection of infertility in males and in the screening of human populations for the presence of such mutation or mutations as a predictive test for male infertility. The present invention further relates to the use of the POLG gene as an indicator of other pathological conditions associated with or related to male infertility, including those manifesting in women.

BACKGROUND OF THE INVENTION

Fertility problems have manifested increasingly in western countries due to a variety of social causes. For example, young couples delay their decision to establish a family for reasons of education and career, and tend to plan for a smaller family size due to the increasing priority placed upon quality of life. Environmental and lifestyle factors may also play a part in revealing an underlying subfertility due primarily to other causes. For many couples, prolonged attempts to become pregnant end in failure, resulting in their seeking assistance from an infertility clinic. This decision is often taken long past the time when they initially would have hoped to start a family. People are understandably reluctant to take a step that may seem humiliating. Such delays, together with the attendant stress, anguish and shame, can have a profoundly destructive effect on relationships and on quality of life generally.

Infertility can result from a great variety of causes, including anatomical, developmental, infectious and toxicological factors. The majority of cases can be attributed wholly or predominantly to one or other partner, with roughly equal numbers of cases of male and female factor infertility. In both instances, however, the primary cause is almost certainly genetic. Estimates of the true population prevalence of infertility vary, but are generally accepted to be in the range of 2 to 5%. This is, therefore, one of the commonest human genetic disorders.

Male infertility can manifest as reduced quantity (oligozoospermia) or total lack (azoospermia) of sperm, reduced quantity of motile sperm (asthenozoospermia) or morphologically abnormal sperm (teratozoospermia). These categories are not exclusive, since many infertile males appear to fall into more than one such class. Microscopic, cytological and biochemical methods are presently available for the determination of these defects. However, actual measurements can be highly variable, even for a single individual between samplings. Frequently, moreover, no actual cause for male infertility can be found. This can cause additional costs arising from the need for further clinical examinations. Selecting an appropriate method of assisted reproduction is often a haphazard and costly matter, with no guarantee of eventual success. All these difficulties and delays can place severe, additional strains on relationships. Additional means for the early detection or prediction of infertility, in particular male infertility are thus needed.

Early detection of male infertility would save both money and human stress and would allow appropriate counselling or assisted reproduction to be offered to a significant population of individuals who would otherwise only discover their problem after it has caused severe damage to their quality of life.

Though it has been long suspected that male infertility in most cases is a genetic disorder, and furthermore that it is genetically heterogeneous (i.e. that many different genes are the underlying cause of the disorder in different individuals), little information has emerged relating specific genetic defects and male infertility. The two known genetic causes of male infertility are the 'cystic fibrosis' mutations in the CFTR gene, part of a clearly recognizable clinical syndrome affecting approximately one person in 1500 [see, e.g. Lissens, W. and Liebaers, I. Baillieres Clinical Obstetrics and Gynaecology 11 (1997) 797–817; Schnedl, W. et al., Wiener Klinische Wochenschrift 103 (1991) 29–33] and a deletion on the Y chromosome, that leads to complete azoospermia, and is found in approximately 1 to 2% of infertile males in this category [Elliott, D. J. and Cooke, H. J. BioEssays 19 (1997) 801–809]. The supposed genetic cause of male infertility in the vast majority of cases has thus far remained unknown.

Since spermatozoa are heavily dependent on respiratory energy for motility, impaired energy metabolism, whether in mature spermatozoa or at earlier stages of male germ cell differentiation, is a long hypothesized mechanism contributing to infertility. Defects in mitochondrial function [Johns, J. C. S. et al., Nat Med 3 (1997) 124–125], possibly associated with mtDNA lesions [Kao, S. H. et al., Mol Hum Reproduction 4 (1998) 657–666; Lestienne P. et al., Mol Hum Reproduction 3 (1997) 811–814], have been reported in sperm samples from infertile males, and sperm motility appears to be correlated with mitochondrial respiratory activity [Ruiz Pesini, E. et al., Clin Chem 44 (1998). 1616–1620] and membrane potential [Troiano. L. et al., Exp Cell Res 241 (1998) 384–393]. However, no relationship between a specific mitochondrial gene and male infertility has been disclosed or even suggested.

SHORT DESCRIPTION OF THE INVENTION

It has now, surprisingly, been discovered that the frequency of a mutant genotype in the POLG gene encoding the catalytic subunit of mito-chondrial DNA polymerase (DNA polymerase γ) is significantly increased in groups of infertile males. Specifically, the mutant genotype has been located in the area of the trinucleotide (CAG) microsatellite repeat of the POLG gene within the N-terminal region of the coding sequence. While the normal POLG gene contains 10 consecutive, glutamine encoding CAG codons, followed by a single CAA and two further CAGs, at least one allele with an altered CAG repeat-length in the POLG gene is found in a large population of infertile men.

The POLG mutations described in the present application represent the first significant step in efforts of elucidating the genetic nature of male infertility and provide novel means of diagnosis thereof.

An object of the invention is thus to provide a non-invasive, non-intrusive diagnostic method that is useful in identifying, detecting and characterizing male infertility in the large fraction of cases where its causes remain unsolved.

A second object is to provide a simple screening test of strong predictive value, in order to identify in advance those individuals who will require reproductive counselling and assistance. Such information will greatly enhance the expected quality of life of those who suffer from this disorder.

The present invention relates to a new method for the diagnosis of male infertility by detecting the presence or absence of a mutation or mutations in the POLG gene encoding the catalytic subunit of mitochondrial DNA polymerase in a biological sample.

The present invention also relates to the use of a mutant form of the POLG gene encoding the catalytic subunit of mitochondrial DNA polymerase for the diagnosis of male infertility.

The present invention also relates to the use of a mutant form of the POLG gene encoding the catalytic subunit of mitochondrial DNA polymerase as a diagnostic agent.

The present invention further relates to diagnostic kits containing suitable reagents to detect a mutant form of the POLG gene or the normal POLG gene.

The present invention further relates to the use of the POLG gene as an indicator of other pathological conditions associated with or related to male infertility, including those manifesting in women.

DETAILED DESCRIPTION OF THE INVENTION

Figure 1:
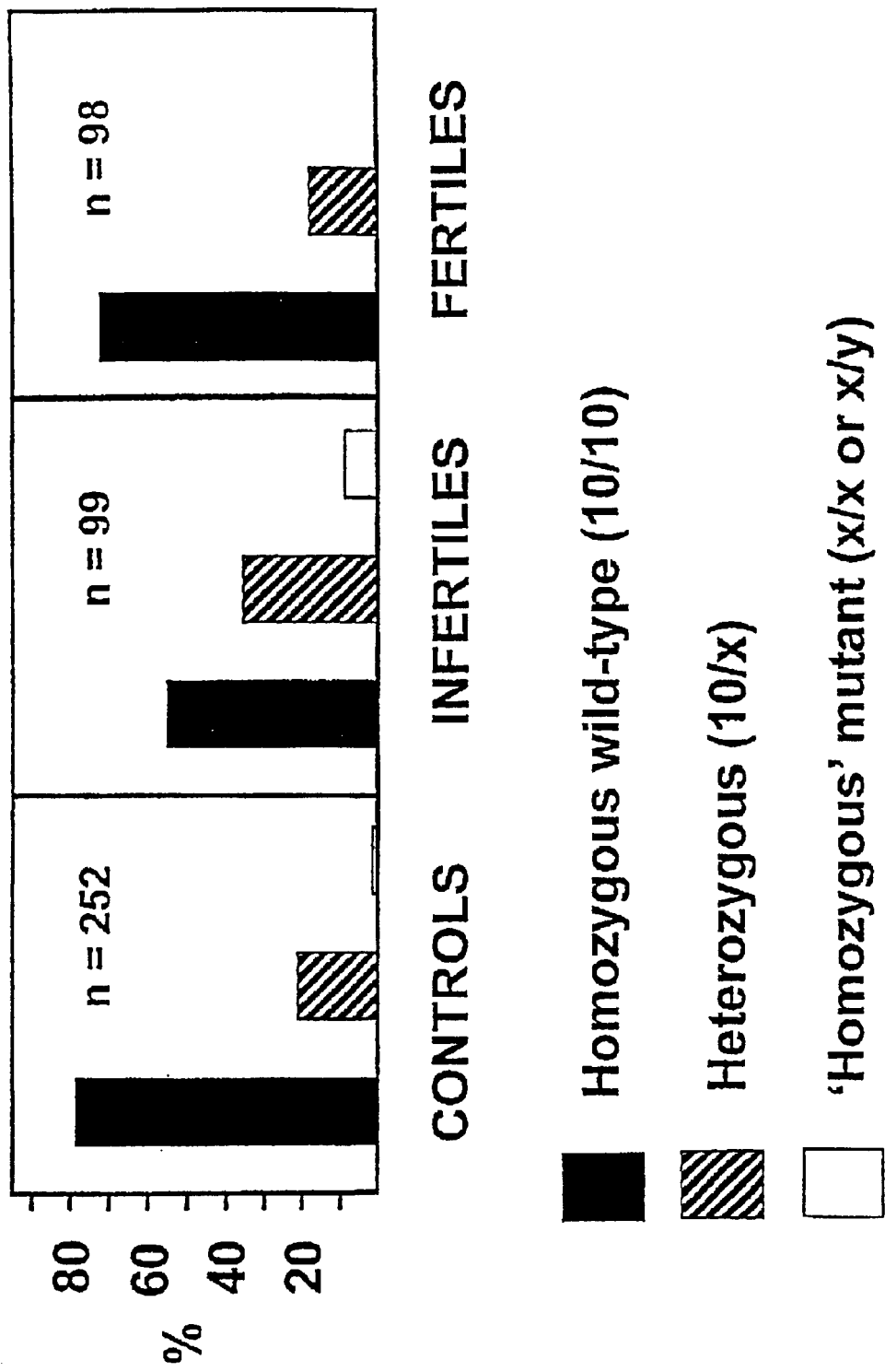
FIG. 1 illustrates the genotype data of Table 2 as a bar chart.

Microsatellite sequences (short sequences consisting of consecutive runs of a simple repeated element, such as a di- or trinucleotide) are well established sources of genetic polymorphism, exhibiting significant levels of length variation in the many genetic loci where they are found. This reflects the fact that they are inherently less stable than other sequences during, for example, DNA replication or repair, where slippage mis-pairing events may increase or decrease the number of re-iterated units. Many such sequences are found within the human genome, and are usually located outside of coding regions, where they have little consequence for phenotype. In some instances, however, they are located within or adjacent to coding DNA. In these cases, large expansions of the number of repeat units can have a profound effect, leading to loss or gain of genetic function and a resulting pathological phenotype. Instability at trinucleotide repeats is already known to be associated with various human disorders, including, for example, Huntington's disease (HD), myotonic dystrophy (DM), and several forms of spinocerebellar atrophy (e.g. SCAI). Other, more subtle variations at trinucleotide microsatellites can also affect phenotype, and the association described herein, between male infertility and variation in the CAG trinucleotide tract of the POLG gene, encoding the catalytic subunit of mitochondrial DNA polymerase, falls into such a category.

Rovio, A. et al. studied the frequency of different repeat-length alleles of the POLG gene in control populations, as well as in groups of patients suffering from recognized mitochondrial disorders (Eur J Hum Genet, 1999 in press). The predominant allele of 10 CAG repeats was found at a very similar frequency (approximately 88%) in both Finnish and ethnically mixed population samples, with homozygosity close to the equilibrium prediction of 80%. Other alleles of between 5 and 13 repeat units were detected, but no larger, expanded alleles were found. Patients with a variety of molecular lesions in mtDNA showed no differences in POLG trinucleotide repeat-length distribution from controls. The authors concluded that their findings rule out POLG repeat expansion as a common pathogenic mechanism in disorders characterized by mitochondrial genome instability.

The present invention is based on studies that were designed to test a hypothesis that this gene, encoding a major component of the machinery of mitochondrial DNA maintenance, is involved in infertility, via impaired energy metabolism of spermatozoa. The POLG gene encodes a protein of approximately 130 kDa and has been mapped to the region of chromosome 15q24–15q26 [Walker, R. L. et al., Genomics 40 (1997) 376–378; Ropp, P. A. and Copeland, W. C., Genomics 36 (1996) 449–458; Zullo, S. J. et al., Cytogenet Cell Genet 78 (1997) 281–284].

For PCR analysis, nested primers flanking the POLG CAG repeat were designed, based on a region of the coding sequence of POLG (see sequence id. no. 1). The primers amplified the predicted fragments from genomic DNA, as verified by direct sequencing. Testing against the monochromosomal interspecies hybrid and Genebridge 4 radiation hybrid panels [Gyapay, G. et al, Hum Mol Genet 5 (1996) 339–346] confirmed that they detected only the expected gene sequence from chromosome 15q, and not a pseudogene. The 5' primer (also designated mip51) was also found to generate the predicted products, using other, more downstream 3' primers from the same exon of the POLG gene. Using these primers and sperm DNA from individuals in whom azoospermia was excluded, the PCR analysis showed that 9 out of 99 male infertiles were homozygous for absence of the normal, 10 repeat-unit allele. Thus approximately 10% of infertile males, whose infertility is not clearly attributable to known causes, and excluding cases of azoospermia, completely lacked the common POLG allele, having 10 consecutive CAG codons. Instead they possessed two alleles with a different number of CAG repeats. No instances of this genotype were found in sperm DNA from 98 fertile males. The association is highly significant based on two different statistical tests (the z-test for percentages, as well as Poisson probabilities). The homozygous mutant genotype was found in only 2 of over 250 healthy controls collected without regard to gender or fertility.

Male infertiles also showed a higher frequency of heterozygosity than found amongst fertile males or in the general population. Some 35% of infertile males, compared with only about 20% in the fertile or unselected population, were heterozygous at the POLG CAG repeat, i.e. possessed one copy of the wild-type or normal allele with 10 repeats, and one other copy. These figures strongly indicate that many of the 35% of infertiles who are heterozygotes are, in fact, compound heterozygotes, i.e. that the allele of the POLG gene that is apparently wild-type or normal at the CAG repeat in fact carries a mutation elsewhere in the gene, such that both copies are defective, at least as regards the function that POLG performs in spermatogenesis that is required for fertility.

PCR studies of POLG genotype frequencies in blood DNA from various categories of patients indicated that a mutation at this locus is not associated with azoospermia or with severe oligozoospermia, but is found in individuals with a range of sperm quality defects.

Also fluorescent PCR using custom primers was used to genotype all individuals in the study for POLG CAG repeat length, as summarized in Table 2. Semen DNA from a minority (approx. 15%) of male infertiles yielded no clear signal and these were excluded from consideration. Approximately 10% of individuals lacked the normal allele. By contrast, this normal allele was present in all 98 fertile males studied. The normal allele was also absent in only one out of 118 healthy male controls, which had not been selected on the basis of fertility, in addition to the 250 controls studied previously without regard to gender or fertility.

Given that the combined frequencies of mutant alleles (i.e. those having any number of repeats other than 10) revealed in the population survey of Rovio, A. et al. (supra) was 0.12, the homozygous mutant genotype is expected to be found in approximately 1.5% of randomly selected individuals, based on standard Hardy-Weinberg predictions (see Table 2). The above data indicate that it was found in the general population slightly below expectation (0.8%, i.e. 2 out of 252), although this devlaton is not statistically significant. By contrast, finding the homozygous mutant genotype by chance in 9 out of 99 individuals is exceedingly unlikely, assuming that the previously measured allele frequencies are representative. The association is significant (p<0.01) based on a z-test for percentages (comparing fertile and infertile groups), or using Poisson statistics (assuming a mean population frequency of the homozygous mutant genotype of 1.5%).

Many different alleles and combinations thereof were found in individuals lacking the common allele (Table 1). This indicates that it is the absence of the normal allele, rather than the presence of a particular alternate allele, that is associated with the phenotype. All alleles found in infertiles were also found in controls. The frequencies, relative to one another, of the various mutant alleles found amongst infertiles were also similar to those found in the general population. The different profiles of POLG genotypes found in sperm DNA from fertile and infertile males, compared with controls, is illustrated in FIG. 1. 35 out of 99 (i.e. 35%) of infertiles were heterozygotes, carrying just one copy of the normal allele.

This is well above expectation (21%), based on the measured allele frequencies in the overall population, or compared with the fertile control group (18%). Importantly, some of these could represent compound heterozygotes, with a second mutation mapping elsewhere in the gene than within the CAG repeat of the coding region of the gene.

In order to establish the type of infertility associated with POLG genotype, blood DNA was studied from two larger groups of patients, who included a high proportion of azoospermic individuals and those with severe oligozoospermia (sperm concentration<5×106/ml), as well as individuals with only a mild abnormality of sperm concentration, motility and/or morphology. Sperm DNA was also analyzed from a further set of patients, for whom extensive phenotypic data were available, and which consisted of cases of 'pure asthenozoospermia', with sperm concentrations well into the normal range (generally>100× $10^6$/ml).

Cases lacking clear results of sperm analysis were excluded, as were those where clinical or karyotypic examination clearly indicated an established hormonal, developmental or traumatic etiology of their infertility. The azoospermic and severe oligozoospermic patients were considered separately from those having sperm concentrations of $5 \times 10^6$/ml or greater.

Out of 62 azoospermic and 73 severe oligozoospermic individuals, no cases of homozygous absence of the normal allele were detected. The frequency of heterozygotes in these groups (30%) was, however, slightly above the population average. By contrast, 8 out of the 113 with infertility of unknown etiology, and having measured sperm concentrations of $5 \times 10^6$/ml or greater, lacked the normal allele.

Individuals homozygous for the absence of the normal allele were found in every category of sperm quality defect (sperm number, motility or morphology, or any combination). Most, however, were at or below at least two of the thresholds commonly used to define oligozoospermia ($20 \times 10^6$ sperm/ml), asthenozoospermia (50% motile sperm) and teratozoospermia (10% morphologically normal spermatozoa). However, no mutant genotype was found in semen DNAs from the 56 patients with 'pure asthenozoospermia'. It is concluded that the mutant POLG genotype is associated with a general impairment in sperm quality and/or number, but neither with the complete or almost complete absence of spermatozoa, nor with a motility defect as such. The simplest interpretation is that cell division or differentiation is impaired, leading to a low production of normal spermatozoa.

The above data clearly indicate that POLG alleles other than the normal one of 10 repeat units are deleterious to sperm function or differentiation, but have little or no effect on other tissues. Polyglutamine tracts are commonly regarded as interfaces for protein-protein interactions, hence it is possible that a sperm-specific protein interacts with this region of the polypeptide. Other possibilities are that repeat-length variants are inherently unstable, poorly targeted to mitochondria, or enzymatically defective, all of which are testable. The many rounds of cell division during spermatogenesis, plus the necessity, for the creation of functional spermatozoa, of maintaining a genetically fit mitochondrial genome, argue that a sub-optimal mtDNA polymerase, whether by virtue of impaired fidelity, processivity, or some other defect, could result in the accumulation of mtDNA mutations and failure to complete differentiation.

Male infertility is certainly a genetically heterogeneous disorder [Sokol, R. Z., Curr Opinion Obst Gynaecol 7 (1995) 177–181]. The data of the present invention indicate that where there is no other obvious etiology, approximately 10% and perhaps as many as 20% of cases are associated with a mutant genotype at the POLG locus, excluding those where sperm count is negligible.

The measured frequency of mutant alleles in the population (approx. 0.12) means that approximately 1.5% of all males will lack the normal allele, and are predicted to be infertile or at least subfertile, based on these findings.

According to the diagnostic method of the present invention, the presence or absence of a mutation or mutations in the POLG gene can be detected from a biological sample by any known detection method suitable for the purpose. Thus, the presence or absence of a mutation or mutations in the POLG gene can be detected from a biological sample by any known method for detecting gene copy number or expression, i.e. methods based on detecting the copy number of the gene (or DNA) and/or those based on detecting the gene expression products (mRNA or protein). Such methods are easily recognized by those skilled in the art and include the use of the polymerase chain reaction (PCR) or other thermal cycler-based DNA synthetic techniques in the presence of appropriate oligonucleotide primers specific for the POLG gene, molecular cloning in a plasmid or other suitable vector, detection of length variants in a DNA sample by agarose or polyacrylamide gel electrophoresis or any analogous technique, gel or capillary electrophoresis with automated detection and analysis of products tagged with a fluorescent or other label incorporated into the DNA, DNA sequence determination by any technique, heteroduplex-based and associated methods for detecting base mismatches or length variants, mass spectroscopy, chromatographic and other separation methods, Western analyses, immunohistochemistry, and other immunoassays, and any technique suitable for the detection and functional characterization of nucleic acid and protein which may be applied in mutational analysis. Preferable methods are those suitable for use in routine clinical laboratories, or which may eventually be developed in self-test kits.

In the diagnostic method of the invention, the biological sample can be any suitable tissue sample or body fluid, such as buccal smear (mouthwash), hair roots, semen, seminal plasma, whole blood, serum or plasma, or cultured cells derived from any biopsy. The biological sample can be, if necessary, pretreated in a suitable manner known to those skilled in the art, for the purposes of extraction of DNA in a form suitable for analysis.

The diagnostic kit of the present invention comprises reagents necessary for the detection of a mutation or mutations in the POLG gene. These reagents include specific antibodies, preferably monoclonal antibodies, capable of identifying the POLG gene or its gene products, other antibodies, primers, markers and/or standards that are needed for visualization or quantification as well as buffers, diluents, washing solutions and the like, commonly contained in a commercial reagent kit. Alternatively, the diagnostic kit of the present invention may comprise portions of the POLG gene or its functional variant or fragment, or other nucleic acid-derivative related to it, together with suitable reagents, such as those listed above, needed for the detection of the mutation or mutations in the POLG gene.

The present invention provides an additional means for detecting and analyzing male infertility, and a means for predicting it, when carried out on adults, children, in infancy, in utero or during embryonic development.

The invention is now elucidated by the following non-limiting examples. The patients and controls used in the first example are as follows. Volunteers for the study, as authorized by the local ethical committee, were recruited from amongst male infertiles attending an infertility clinic in Oxford. Semen samples obtained by masturbation were stored frozen in liquid nitrogen for further study. Azoospermic individuals (approx. 20% of the total) were excluded, as were any for whom a clear, established etiology (hormonal, developmental, karyotypic or traumatic) could be found to account for their infertility. Semen was also collected from sperm donors, for use as fertile controls in the study. Semen or seminal plasma was also provided from similarly defined infertile males in Tampere, Finland, and from infertiles in Australia and Taiwan. Blood samples were provided from fertile and infertile males, as well as from unselected control males in Düsseldorf, Germany, and from male infertiles in Edinburgh, Scotland. Blood samples were also provided by otherwise healthy volunteers amongst laboratory personnel and associates, who were not screened for fertility.

EXAMPLE 1

Genotyping at the POLG CAG Repeat as a Diagnostic Test for Male Infertility

DNA was prepared from fresh or frozen sperm or seminal plasma as follows. 400 $\mu$l samples were micro-centrifuged at 13,000 rpm for 5 min and the pellets washed twice with phosphate buffered saline, pH 7.4 (PBS). Crude DNA was then extracted from the washed pellets by incubating with proteinase K as described by Reid, F. M. et al. [Hum Mutation 3 (1994) 243–247], followed by inactivation of the enzyme at 92° C. for 10 minutes. Blood DNA was isolated by the same method, as described by Reid, F. M. et al., supra. DNA can be obtained from other biological samples using essentially similar methods which are well known to those skilled in the art. Prior to all PCR analyses, the DNA extracts were microcentrifuged for 15 sec and 0.5 $\mu$l of clear lysate used as template. In any cases where signals were low or uninterpretable, PCR was repeated using 0.5 $\mu$l of the template DNA solution diluted to various extents in order to reduce the concentration of contaminants that may inhibit DNA synthesis. More than 0.5 $\mu$l of template DNA solution may also be used, if sample concentration is judged to be too low.

Fluorescent PCR analysis of POLG genotype was carried out as follows. Nested oligonucleotides corresponding to regions of the N-terminal coding sequence of POLG, as indicated in the accompanying list of sequences, were purchased from Life Technologies (Paisley, Scotland) and DNA Technology (Aarhus, Denmark). One of the primers, mip51 (5' CCAGCTCCGTCCCCGCGTCCGACC 3'; sequence id. no. 2), was 5' prelabeled with the fluorescent dye ROX (PerkinElmer) by the manufacturer, but other dyes of similar application can also be used.

Fluorescent PCR reactions used, at 0.2 mM each, ROX-labeled primer mip51 plus one downstream primer, unlabelled, either mip31 (5' GCTGCCCGCCCTCCGAG-GATAGCAC 3'; sequence id. no. 3; generating a 126 bp PCR product from the wild-type allele, when used in combination with primer mip51), mip32 (5'CTCTCGAGAGCATCTGGATGTCCMTC 3'; sequence id. no. 4; generating a 165 bp PCR product from the wild-type allele, when used in combination with primer mip51) or mip33 (5'CTCGTGCAGCCCTCTCGAGAGCAT 3'; sequence id. no. 5; generating a 176 bp PCR product from the wild-type allele, when used in combination with primer mip51). Reactions were carried out in 12.5 $\mu$l at 200 $\mu$M dNTPs (Pharmacia Biotech, Sweden), plus an appropriate quantity of a suitable thermostable DNA polymerase (0.15 units of Dynazyme, from Finnzymes, Espoo, Finland) in the manufacturer's buffer. Reactions comprised 30 cycles of denaturation for 1 min at 95° C., annealing for 45 sec at 62° C., and extension for 1 min at 72° C. (a 5 min extension in final cycle). Products were diluted 1:10 in water, and samples containing 1 $\mu$l of diluted PCR product, 12 $\mu$l of deionized formamide and labelled DNA fragment size markers in the appropriate size range were added [e.g. 0.15 $\mu$l of Tamra Genescan350 DNA size standards (Perkin Elmer)], and samples were analyzed by capillary electrophoresis on a suitable electrophoresis/fluorescent analysis instrument, e.g. ABI 310 Genetic Analyzer (PerkinElmer), using the manufacturer's data collection and analysis software.

Samples giving ambiguous or low signals, or those giving a result indicative of a mutant genotype, were re-evaluated using a second downstream primer. In all analyses, a reaction using a template DNA sample previously demonstrated to contain only the wild-type POLG allele, as well as a reaction run without any added DNA, were run alongside as positive and negative controls, respectively.

The results showing the mutant POLG alleles of male infertiles are shown in Table 1.

TABLE 1

Mutant POLG alleles of infertile males

| POLG repeat-length genotype | Number |
|---|---|
| 11/11 | 8 |
| 11/12 | 5 |
| 11/9 | 3 |
| 9/12 | 2 |
| 11/13 | 1 |
| 9/9 | 1 |
| 8/11 | 1 |
| 8/12 | 1 |
| 6/12 | 1 |
| Total | 23 |

The PCR amplification and fluorescent analysis described enabled samples to be categorized as follows:

Class I—WILD-TYPE (or normal) HOMOZYGOTES: only a single allele was detected, as a clean peak of a size consistent with the presence of 10 consecutive copies of the CAG repeat.

Class II—MUTANT 'HOMOZYGOTES': one or two alleles were detected, both corresponding with length variants other than the wild-type allele of 10 CAG repeats. These individuals are compound heterozygotes at the POLG CAG repeat. However, since such individuals are homozygous for loss of the wild-type allele, they are placed in a different category from 'true' heterozygotes as defined below (Class III).

Class III—HETEROZYGOTES: two length alleles were detected, one corresponding with the wild-type allele (10 CAG repeats) and the other a different number.

Data for such an analysis are illustrated in FIG. 1 and Tables 2 and 3, below. Controls were the combined sets collected previously from Finland, being a mixture of Finns plus other ethnic groups of both sexes, plus those from Germany (males only, no selection based on fertility). Infertiles and fertiles indicated in Table 2 each represent pooled groups of individuals from Finland and England.

TABLE 2

POLG genotype frequencies detected in various fertile and infertile males (sperm), plus unselected controls (blood)

| Patients (COUNTRY) | Class I: wild-type homozygotes | Class II: mutant 'homozygotes' | Class III: heterozygotes |
|---|---|---|---|
| Infertile males (FIN/ENG) | 55 (56%) | 9 (9%) | 35 (35%) |
| Fertile Males (FIN/ENG) | 80 (82%) | 0 (0%) | 18 (18%) |
| Total controls (FIN/ENG/D) | 195 (77%) | 2 (1%) | 55 (22%) |

TABLE 3

Frequency of 'mutant homozygotes' (Class II) in various groups of infertile males

| Patients (COUNTRY, DNA SOURCE) | Total analysed | Class II: mutant 'homozygotes' |
|---|---|---|
| Azoospermia or severe oligozoospermia (sperm concentration < 5 × 10⁵/ml) (D/SCO, blood) | 135 | 0 (0%) |
| Pure asthenozoospermia (<50% motile, normal sperm concentrations) (Taiwan, sperm) | 55 | 0 (0%) |
| Combined sperm quality defect (2 or more of moderate oligozoospermia, asthenozoospermia, and teratozoospermia) (D, blood) | 113 | 8 (7%) |

The analysis resolved the samples into the following groups in a clearly predictive manner, as follows.

(1) Genotype frequencies in the control group were very close to the equilibrium predictions based on overall population-based measurements of allele frequencies of 0.88 (wild-type, 10 CAG repeats) and 0.12 (all mutant alleles combined).

(2) No instances of 'mutant homozygotes' (Class II) were detected amongst fertile males.

(3) Approximately 9% of infertile males, excluding cases of azoospermia and severe oligospermia, fell into Class II.

(4) Heterozygotes (Class III) were found in all groups, but at a higher frequency in infertile than fertile males or controls.

The diagnostic and counselling implications of the test for POLG genotype that forms the subject of the present invention, and as proposed to be carried out, for example, in an infertility clinic, are as follows:

(1) A result falling into Class II is an indicator of a specific type of male factor infertility, associated with POLG dysfunction. This genotype is never found in fertile males. Other clinical or biochemical investigations of both partners can essentially be dispensed with as unnecessary. Even in the absence of sperm quality data, it indicates that intra-uterine insemination and probably IVF are likely to fail, and that recourse to ICSI (intra-cytoplasmic sperm injection) is advisable.

(2) A result falling into Class I does not exclude male factor infertility of other types, nor any other diagnosis.

(3) A result falling into Class III is ambiguous, and warrants further genetic investigation of the POLG locus, as illustrated below (example 2).

EXAMPLE 2

Complete Analysis of the POLG Gene as a Diagnostic Test for Male Infertility

Results from the type of analysis illustrated in Example 1 are necessarily ambiguous in the case of individuals who prove to be heterozygous at the POLG gene CAG repeat (i.e. who possess one copy of the wild-type, 10-repeat allele, plus one copy of some other length variant). In these cases, further investigation is warranted, in order to establish whether they represent cases of true heterozygotes (one fully functional, one mutant copy of the gene), as found amongst fertile males and controls, or whether they represent compound heterozygotes carrying one copy of the gene mutated within the POLG CAG repeat tract, and a second copy which has a pathological mutation elsewhere in the gene. The present invention thus covers not only the use of genotyping at the CAG repeat, but also the complete sequencing of the POLG gene as a diagnostic procedure for the determination of male infertility associated with POLG gene dysfunction, in cases where genotyping at the CAG repeat is insufficient to permit an unambiguous molecular diagnosis. Because such cases are expected to constitute up to half of all individuals with POLG-associated infertility, based on the observed frequencies of homo- and heterozygotes, i.e. given the excess number of heterozygotes amongst the infertiles, the further analysis illustrated in this Example will have an important diagnostic value, as regards the counselling and treatment to be offered.

DNA is prepared from the same sources and using the same methods as indicated under Example 1 (above). Long-extension PCR is carried out using a series of primer pairs flanking blocks of exons of the POLG gene creating products that include the entire coding region of the gene, the 5' and 3' untranslated segments of the POLG mRNA, the proximal promoter of the gene, and all intron/exon boundaries. Oligonucleotide primers are based on the publicly available sequence of the POLG gene (deposited in the Genbank database as accession number AC005317), and sourced from companies such as indicated under Example 1. In this specific example the relevant segments of the POLG gene are amplified initially as 3 large PCR products, although many other strategies are equivalent, based on other combinations of primers according to the database sequence. LX-PCR is carried out with a standard reagent kit (e.g. Boehringer Mannheim Extend DNA Polymerase) under manufacturer's recommended conditions or using equivalent materials sourced elsewhere. PCR products are analysed by agarose gel electrophoresis and purified from agarose gels by standard, spin-column methods, e.g. using kits available from Qiagen or similar manufacturers. A total of 52 sequencing primers are also required (one in each direction for the 21 short exons and boundaries, two in each direction to cover the longer exon 23, and three in each direction to cover the longest exon, exon 2, in which the CAG repeat lies, presenting additional difficulties. The 20 bp sequences of these correspond with intronic sequences located approximately 30 bp up- and downstream of the various intron-exon boundaries, based on the database-deposited gene sequence. In addition, internal exonic sequencing primers (one for each strand) are required for 20 bp regions in the middle of exon 23 and exon 2, as well as 20 bp on either side of the CAG repeat (one strand only. In each case, reading towards the repeat.

Fluorescent DNA sequencing is carried out using a standard dye-terminator reagent kit (e.g. PerkinElmer Big Dye) in thermal cycling reactions using the long PCR products as template and each sequencing primer as appropriate under the kit manufacturers recommended conditions. Sequencing reaction products are analyzed by gel or capillary electrophoresis, on a suitable electrophoresis/fluorescent analysis instrument, e.g. ABI 310 Genetic Analyzer (PerkinElmer), using the manufacturer's data collection and analysis software.

DNA sequences are carefully examined for evidence of 3 types of detectable heterozygosity, which manifest differently on the sequence traces, as follows. (a) A heterozygous point mutation manifests as a specific ambiguity localized to one nucleotide pair and detectable on both strands in a congruent manner (i.e. the specific ambiguity on one strand is found as the exactly complementary ambiguity on the other). (b) A heterozygous deletion or insertion of one or more nucleotides in a localized region manifests as a break-point between a sequence that is readable (unambiguous) and a sequence that is totally unreadable (ambiguous at virtually every position), with the exact location and size of the deletion or insertion inferred by the positions at which ambiguity commences when read on the two strands. (c) A large heterozygous deletion or insertion less than 10 kb in size, with both break-points located within the gene, is evident from heterogeneity in the product sizes in long PCR, with a need to sequence the two alternate products independently to infer the nature and location of the re-arrangement.

A heterozygous deletion or insertion longer than 10 kb or with only one break-point located within the gene does not necessarily manifest in a simple manner by such methods, but can be detected by the use of restriction mapping combined with Southern blotting, or by so-called one-sided PCR methods, in which the flanking regions of a given sequence in genomic DNA are characterized by restriction digestion, dilution, religation to form circles, and PCR using two adjacent, outwardly oriented primers.

Where evidence of a heterozygous mutation is obtained, some form of haplotype analysis is still required to confirm that the CAG repeat-length mutation and the additional heterozygous mutation are on different copies of the gene. This requires a combination of standard mutation detection methods, such allele-specific PCR, or restriction fragment length polymorphism applied over a considerable length of genomic DNA, involving, for example, long-extension PCR or Southern blotting or a combination of such techniques.

The implications of the results from this much more exhaustive test are similar to those outlined under example 1. Assignment of a mutation may not be straightforward, but POLG mutations that cause changes of reading frame, that destroy splice sites or create new ones, that generate a stop codon, that alter a highly conserved amino acid or that delete or interrupt a significant region of coding sequence are unquestionably of pathological significance, if combined with CAG repeat-length mutation in the other copy of the gene.

Detection of a second, clearly pathological mutation in such an individual, outside of the CAG repeat, would confirm that his infertility is of essentially the same kind as those already discussed under example 1, with similar implications for counselling and treatment.

EXAMPLE 3

Application of the Invention to Population-based Screening for Genetic Predisposition to Infertility This example describes the way in which the invention is to be applied in the context of genetic screening of the population. It is assumed that this application will respect privacy, plus any relevant legislation in force in different jurisdictions. Its goal is to enable people to make informed choices about their reproductive life without prescribing to them any particular course of action. The possibility for a male to know, in advance, that he will suffer infertility at reproductive age, empowers both him and his partner in a way that other kinds of clinical testing do not, given that they are typically applied long after the problem has manifested and usually too late for its consequences to be completely corrected or managed. This application could be placed in the context of a programme of voluntary genetic testing applied in infancy, or at any age, being offered as one of a large number of tests for genetic disorders. It could also be in the context of a confidential advisory service or even, eventually, a self-test kit. The specific example given is in the context of a voluntary public health programme focused on the specific question of genetic predisposition to infertility and offered in early adolescence.

A defined population of young males (e.g. all those reaching their 17th birthday in a given year in a given locality) are contacted via family doctors, educational institutions or a population registry and asked whether they wish to participate voluntarily in the screening programme under conditions of total confidentiality. The benefits of choosing to do so, plus the predictive limitations of the test, are fully explained to all enabling them to make an informed choice about their participation. Buccal smears (mouthwash samples) are collected from those agreeing to take the test, and DNA is extracted using similar methods as outlined under example 1. POLG genotyping is carried out using the same techniques as outlined in examples 1 and 2 above. The results of the test are communicated to all volunteers on a confidential basis, with more specific counselling offered to anyone who requests it.

The test results and their implications are clear those found to be homozygous for loss of the wild-type POLG repeat-length allele, or to be compound heterozygotes with one copy of the gene mutated at the CAG repeat and one copy carrying a clearly pathological mutation elsewhere in the gene, are advised that prior genetic surveys indicate that they will suffer from a fertility problem, and that if they wish to have children they should consult an infertility clinic at the appropriate time to arrange for assisted reproduction as already described under example 1. Those found to carry at least one wild-type copy of the gene are advised that one common, genetic cause of male infertility has been excluded, but that this does not necessarily mean that they will be free of fertility problems, since there are other genetic and environmental causes that account for a large fraction of fertility problems. Hence they should be aware of the relevant services available in their locality, and advised to seek specific advice if they become aware of a fertility problem in the future.

Obviously, the value of the test described in this example will be greatly enhanced, if combined in the future with tests for other genetic predispositions to male infertility, as these become apparent. This will strengthen the predictive value of the test, although even those in whom all genetic causes of male infertility have been excluded must be made aware that their partner may also suffer fertility problems independently, and that genetics cannot explain everything.

What is claimed is:

1. A method for diagnosis of male infertility, comprising:
   (a) detecting in a sample obtained from a male patient, wherein said male patient is suspected of suffering from infertility and has two alleles of the POLG gene encoding the catalytic subunit of mitochondrial DNA polymerase, the presence or absence of at least one trinucleotide (CAG) microsatellite repeat-length mutation in one allele of the POLG gene and
   (b) detecting the presence or absence of at least one pathological mutation in the coding region of another allele of the POLG gene in said sample; wherein the presence of at least one mutation in both alleles of said POLG gene is indicative of male infertility.

2. A method of screening for genetic predisposition to male infertility, comprising:
   (a) detecting in a sample obtained from a male patient, wherein said male patient is suspected of suffering from infertility and has two alleles of the POLG gene encoding the catalytic subunit of mitochondrial DNA polymerase, the presence or absence of at least one trinucleotide (CAG) microsatellite repeat-length mutation in one allele of the POLG gene and
   (b) detecting the presence or absence of at least one pathological mutation in the coding region of another allele of the POLG gene in said sample; wherein the presence of at least one mutation in both alleles of said POLG gene is indicative of genetic predisposition to male infertility.

3. A method of claim 1, wherein mutations are located in both alleles of the POLG gene in the trinucleotide (CAG) microsatellite repeat of the POLG gene.

4. A method of claim 2, wherein mutations are located in both alleles of the POLG gene in the trinucleotide (CAG) microsatellite repeat of the POLG gene.

5. A method of claim 1, wherein the at least one mutation in another allele of the POLG gene is located in or near a coding region of the POLG gene.

6. A method of claim 2, wherein the at least one mutation in another allele of the POLG gene is located in or near a coding region of the POLG gene.

7. A method of claim 1, wherein detection of at least one mutation is performed by a gene-technological method.

8. A method of claim 7, wherein the detection of at least one mutation is performed by a gene-technological method selected from the group consisting of the polymerase chain reaction (PCR) or other thermal cycler-based DNA synthetic techniques, molecular cloning in a plasmid or other suitable vector, detection of length variants in a DNA sample by agarose or polyacrylamide gel electrophoresis, gel or capillary electrophoresis and analysis of products tagged with a fluorescent or other label incorporated into the DNA, DNA sequence determination and any heteroduplex-based or similar methods for detecting base mismatches or length variants.

9. A method of claim 1, wherein the detection of at least one mutation is performed by an immunological method selected from the group consisting of Western analysis, immunohistology and immunoassay, for characterization of a mutant gene or gene product.

10. A method of claim 9, wherein the detection of at least one mutation is performed using immunohistology.

11. A method of claim 2, wherein detection of at least one mutation is performed by a gene-technological method.

12. A method of claim 11, wherein the detection of at least one mutation is performed by a gene-technological method selected from the group consisting of the polymerase chain reaction (PCR) or other thermal cycler-based DNA synthetic techniques, molecular cloning in a plasmid or other suitable vector, detection of length variants in a DNA sample by agarose or polyacrylamide gel electrophoresis, gel or capillary electrophoresis and analysis of products tagged with a fluorescent or other label incorporated into the DNA, DNA sequence determination and any heteroduplex-based or similar methods for detecting base mismatches or length variants.

13. A method of claim 2, wherein the detection of at least one mutation is performed by an immunological method selected from the group consisting of Western analysis, immunohistology and immunoassay, for characterization of a mutant gene or gene product.

14. A method of claim 13, wherein the detection of at least one mutation is performed by immunohistology.

15. A method of claim 1, wherein at least one mutation of the POLG gene is detected with polymerase chain reaction (PCR) or other thermal cycler-based DNA synthetic techniques.

16. A method of claim 2, wherein at least one mutation of the POLG gene is detected with polymerase chain reaction (PCR) or other thermal cycler-based DNA synthetic techniques.

17. A method claim 1, wherein homozygous loss or compound heterozygous loss of wild-type POLG is detected by a gene-technological method.

18. A method claim 2, wherein homozygous loss or compound heterozygous loss of wild-type POLG is detected by a gene-technological method.

19. A method for diagnosis of male infertility using a sample obtained from a male patient, comprising (i) detecting homozygous loss of wild-type POLG which encodes the catalytic subunit of mitochondrial DNA polymerase, wherein both POLG mutant alleles comprise a length of CAG microsatellite repeat other than 10 repeats, or (ii) detecting compound heterozygous loss of wild-type POLG, wherein one POLG mutant allele comprises a length of CAG microsatellite repeat other than 10 repeats and another POLG mutant allele comprises at least one pathological mutation in its coding region, in said sample through a gene-technological method; wherein mutations in both POLG alleles is indicative of male infertility.

20. A method of screening for genetic predisposition to male infertility using a sample obtained from a male patient, comprising (i) detecting homozygous loss of wild-type POLG which encodes the catalytic subunit of mitochondrial DNA polymerase, wherein both POLG mutant alleles comprise a length of CAG microsatellite repeat other than 10 repeats, or (ii) detecting compound heterozygous loss of wild-type POLG, wherein one POLG mutant allele comprises a length of CAG microsatellite repeat other than 10 repeats and another POLG mutant allele comprises at least one pathological mutation in its coding region, in said sample through a gene-technological method; wherein mutations in both POLG alleles is indicative of genetic predisposition to male infertility.

* * * * *

UNITED STATES PATENT AND TRADEMARK OFFICE
CERTIFICATE OF CORRECTION

PATENT NO.         : 6,811,976 B1                                           Page 1 of 1
APPLICATION NO. : 09/913954
DATED                  : November 2, 2004
INVENTOR(S)        : Howard Trevor Jacobs and Anja Tuulikki Rovio It is certified that error appears in the above-identified patent and that said Letters Patent is hereby corrected as shown below:

TITLE PAGE, ITEM (56)
Under "OTHER PUBLICATIONS" -- in the first line, please remove the reference "Rovio et al. Euro. Jrnl. Of Human Genetics (1999) 7, 140-146."

TITLE PAGE, ITEM (56)
In the third line, please remove the reference "Ropp and Copeland Genomics (1996) 36,449-458."

TITLE PAGE, ITEM (56)
In the fourth line, please correct the name "Rovia" to read --Rovio--

Under "DETAILED DESCRIPTION OF THE INVENTION":

In column 13, line 15, please change "The test results and their implications are clear those" to read --The test results and their implications are clear:  those--

Signed and Sealed this

Seventh Day of August, 2007

JON W. DUDAS
*Director of the United States Patent and Trademark Office*

SEQUENCE LISTING

<160> NUMBER OF SEQ ID NOS: 5

<210> SEQ ID NO 1
<211> LENGTH: 4440
<212> TYPE: DNA
<213> ORGANISM: Human

<400> SEQUENCE: 1

```
gcggaccggc cgggtggagg ccacacgcta ccccgaggct gcgtaggccg cgcgaagggg        60
gacgccgtgc cgtgggcctg gggtcggggg agcagcagac cgggaagcac cgtgaggacc       120
gaggatttgg ggtggaaggc aggcatggtc aaacccattt cactgacagg agagcagaga       180
caggacgtgt ctctctccac gtcttccagc cagtaaaaga agccaagctg gagcccaaag       240
ccaggtgttc tgactcccag cgtggggggtc cctgcaccaa ccatgagccg cctgctctgg       300
aggaaggtgg ccggcgccac cgtcgggcca gggccggttc cagctccggg gcgctgggtc       360
tccagctccg tccccgcgtc cgaccccagc gacgggcagc ggcggcggca gcagcagcag       420
cagcagcagc agcagcagca acagcagcct cagcagccgc aagtgctatc ctcggagggc       480
gggcagctgc ggcacaaccc attggacatc cagatgctct cgagagggct gcacgagcaa       540
atcttcgggc aaggagggga gatgcctggc gaggccgcgg tgcgccgcag cgtcgagcac       600
ctgcagaagc acgggctctg ggggcagcca gccgtgccct tgcccgacgt ggagctgcgc       660
ctgccgcccc tctacgggga caacctggac cagcacttcc gcctcctggc ccagaagcag       720
agcctgccct acctggaggc ggccaacttg ctgttgcagg cccagctgcc ccgaagccc       780 ccggcttggg cctgggcgga gggctggacc cggtacggcc ccgaggggga ggccgtaccc       840
gtggccatcc ccgaggagcg ggccctggtg ttcgacgtgg aggtctgctt ggcagaggga       900
acttgcccca cattggcggt ggccatatcc ccctcggcct ggtattcctg gtgcagccag       960
cggctggtgg aagagcgtta ctcttggacc agccagctgt cgccggctga cctcatcccc      1020
ctggaggtcc ctactggtgc cagcagcccc acccagagag actggcagga gcagttagtg      1080
gtggggcaca atgtttcctt tgaccgagct catatcaggg agcagtacct gatccagggt      1140
tcccgcatgc gtttcctgga caccatgagc atgcacatgg ccatctcagg gctaagcagc      1200
```

```
ttccagcgca gtctgtggat agcagccaag cagggcaaac acaaggtcca gccccccaca    1260
aagcaaggcc agaagtccca gaggaaagcc agaagaggcc cagcgatctc atcctgggac    1320
tggctggaca tcagcagtgt caacagtctg cagaggtgca cagacttta tgtaggggg     1380
cctcccttag agaaggagcc tcgagaactg tttgtgaagg gcaccatgaa ggacattcgt    1440
gagaacttcc aggacctgat gcagtactgt gcccaggacg tgtgggccac ccatgaggtt    1500
ttccagcagc agctaccgct cttcttggag aggtgtcccc acccagtgac tctggccggc    1560
atgctggaga tgggtgtctc ctacctgcct gtcaaccaga actgggagcg ttacctggca    1620
gaggcacagg gcacttatga ggagctccag cgggagatga agaagtcgtt gatggatctg    1680
gccaatgatg cctgccagct gctctcagga gagaggtaca agaagaccc ctggctctgg     1740
gacctggagt gggacctgca agaatttaag cagaagaaag ctaagaaggt gaagaaggaa    1800
ccagccacag ccagcaagtt gcccatcgag ggggctgggg ccctggtga tcccatggat     1860
caggaagacc tcggcccctg cagtgaggag gaggagtttc aacaagatgt catggcccgc    1920
gcctgcttgc agaagctgaa ggggaccaca gagctcctgc caagcggcc ccagcacctt     1980
cctggacacc ctggatggta ccggaagctc tgcccccggc tagacgaccc tgcatggacc    2040
ccgggccccg gcctcctcag cctgcagatg cgggtcacac ctaaactcat ggcacttacc    2100
tgggatggct tccctctgca ctactcagag cgtcatggct ggggctactt ggtgcctggg    2160
cggcgggaca acctggccaa gctgccgaca ggtaccaccc tggagtcagc tggggtggtc    2220
tgcccctaca gagccatcga gtccctgtac aggaagcact gtctcgaaca ggggaagcag    2280
cagctgatgc cccaggaggc cggcctggcg gaggagttcc tgctcactga caatagtgcc    2340
atatggcaaa cggtagaaga actggattac ttagaagtgg aggctgaggc caagatggag    2400
aacttgcgag ctgcagtgcc aggtcaaccc ctagctctga ctgcccgtgg tggccccaag    2460
gacacccagc ccagctatca ccatggcaat ggaccttaca cgacgtgga catccctggc     2520
tgctggtttt tcaagctgcc tcacaaggat ggtaatagct gtaatgtggg aagccccttt    2580
gccaaggact tcctgcccaa gatggaggat ggcaccctgc aggctggccc aggaggtgcc    2640
agtgggcccc gtgctctgga aatcaacaaa atgatttctt tctggaggaa cgcccataaa    2700
cgtatcagct cccagatggt ggtgtggctg cccaggtcag ctctgccccg tgctgtgatc    2760
aggcaccccg actatgatga ggaaggcctc tatggggcca tcctgcccca agtggtgact    2820
gccggcacca tcactcgccg ggctgtggag cccacatggc tcaccgccag caatgcccgg    2880
cctgaccgag taggcagtga gttgaaagcc atggtgcagg ccccacctgg ctacacccctt   2940
gtgggtgctg atgtggactc caagagctg tggattgcag ctgtgcttgg agacgcccac     3000
tttgccggca tgcatggctg cacagccttt gggtggatga cactgcaggg caggaagagc    3060
aggggcactg atctacacag taagacagcc actactgtgg gcatcagccg tgagcatgcc    3120
aaaatcttca actacggccg catctatggt gctgggcagc cctttgctga gcgcttacta    3180
atgcagtttta accaccggct cacacagcag gaggcagctg agaaggccca gcagatgtac    3240
gctgccacca agggcctccg ctggtatcgg ctgtcggatg agggcgagtg gctggtgagg    3300
gagttgaacc tcccagtgga caggactgag ggtggctgga tttccctgca ggatctgcgc    3360
aaggtccaga gagaaactgc aaggaagtca cagtggaaga gtgggaggt ggttgctgaa     3420
cgggcatgga aggggggcac agagtcgaaa atgttcaata gcttgagag cattgctacg     3480
tctgacatac cacgtacccc ggtgctgggc tgctgcatca gccgagccct ggagccctcg    3540
```

-continued

```
gctgtccagg aagagtttat gaccagccgt gtgaattggg tggtacagag ctctgctgtt    3600
gactacttac acctcatgct tgtggccatg aagtggctgt ttgaagagtt tgccatagat    3660
gggcgcttct gcatcagcat ccatgacgag gttcgctacc tggtgcggga ggaggaccgc    3720
taccgcgctg ccctggcctt gcagatcacc aacctcttga ccaggtgcat gtttgcctac    3780
aagctgggtc tgaatgactt gccccagtca gtcgcctttt tcagtgcagt cgatattgac    3840
cggtgcctca ggaaggaagt gaccatggat tgtaaaaccc cttccaaccc aactgggatg    3900
gaaaggagat acgggattcc ccagggtgaa gcgctggata tttaccagat aattgaactc    3960
accaaaggct ccttggaaaa acgaagccag cctggaccat agcactgcct ggaggctctg    4020
tatttgctcc cgtggagctt catcggggtg gtgcaggctc ccaaactcag gctttcagct    4080 gtgcttttg caaagggct tgcctaaggc cagccatttt tcagtagcag gacctgccaa    4140
gaagattcct tctaactgaa ggtgcagttg aattcagtgg gttcagaacc aagatgccaa    4200
catcggtgtg gactacagga caaggggcat tgttgcttgt tgggtaaaaa tgaagcagaa    4260
gccccaaagt tcacattaac tcaggcattt catttatttt ttccttttct tcttggctgg    4320
ttctttgttc tgtcccccat gctctgatgc agtgccctag aaggggaaag aattaatgct    4380
ctaacgtgat aaacctgctc caaggcagtg gaaataaaaa gaaggaaaaa aagaaaaaa    4440
```

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
ccagctccgt ccccgcgtcc gacc                                            24

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
gctgcccgcc ctccgaggat agcac                                           25

<210> SEQ ID NO 4
<211> LENGTH: 27
<212> TYPE: DNA
<213> ORGANISM: Artificial Sequence
<220> FEATURE:
<223> OTHER INFORMATION: primer

<400> SEQUENCE: 4
ctctcgagag catctggatg tccaatc                                         27

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
ctcgtgcagc cctctcgaga gcat                                            24